United States Patent
Mizuno (10) Patent No.: US 8,932,206 B2
(45) Date of Patent: Jan. 13, 2015

(54) ENDOSCOPIC APPARATUS AND IMAGE PICKUP METHOD FOR THE SAME

(75) Inventor: Kyosuke Mizuno, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 1433 days.

(21) Appl. No.: 11/881,719

(22) Filed: Jul. 27, 2007

(65) Prior Publication Data

US 2008/0027278 A1 Jan. 31, 2008

(30) Foreign Application Priority Data

Jul. 28, 2006 (JP) ................................. 2006-206830

(51) Int. Cl.
*A61B 1/00* (2006.01)
*A61B 1/045* (2006.01)
*A61B 1/04* (2006.01)
*A61B 1/05* (2006.01)
*A61B 1/06* (2006.01)

(52) U.S. Cl.
CPC ................. *A61B 1/045* (2013.01); *A61B 1/042* (2013.01); *A61B 1/05* (2013.01); *A61B 1/0676* (2013.01); *A61B 1/0684* (2013.01)
USPC ........... 600/109; 600/180; 600/178; 600/179; 348/65; 348/68; 348/297

(58) Field of Classification Search
USPC ................. 600/109, 111, 118, 178, 179, 180; 348/65, 68, 74, 220.1, 221.1, 131, 294, 348/296–297, 302
See application file for complete search history.

(56) References Cited

U.S. PATENT DOCUMENTS

| | | | |
|---|---|---|---|
| 4,803,550 A | | 2/1989 | Yabe et al. |
| 5,134,469 A | * | 7/1992 | Uchimura ........................ 348/68 |
| 6,066,090 A | * | 5/2000 | Yoon .............................. 600/113 |
| 6,489,987 B1 | | 12/2002 | Higuchi et al. |
| 6,734,894 B1 | * | 5/2004 | Higuchi et al. ................. 348/69 |

(Continued)

FOREIGN PATENT DOCUMENTS

| | | |
|---|---|---|
| CN | 201058015 | 5/2008 |
| DE | 202 21 437 U1 | 12/2005 |

(Continued)

OTHER PUBLICATIONS

Kazuya Yonemoto, "6-1-4 Simultaneity in Storage," Basics and Applications of CCD/CMOS Image Sensor, From Principle, Structure, Operation Method, Characteristics, to Summary of System, published in Japan by CQ Publisher, pp. 179 to 180, together with English translation.

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscopic apparatus having an image pickup system operating as follows. Before picking up a still image in a body cavity that almost no light can reach, the system extinguishes LED and resets charges accumulated in respective pixels in a CMOS image sensor. In this reset state, the system illuminates LED and allows the CMOS image sensor to pick up a still image. While the charges are being read from the pixels, the system extinguishes LED and prevents further charges from being accumulated in the pixels from which the charges have not been read yet.

8 Claims, 6 Drawing Sheets

(56) References Cited

U.S. PATENT DOCUMENTS

| | | | |
|---|---|---|---|
| 7,616,238 B2* | 11/2009 | Avni et al. | 348/243 |
| 2002/0158976 A1* | 10/2002 | Vni et al. | 348/243 |
| 2003/0023150 A1* | 1/2003 | Yokoi et al. | 600/300 |
| 2003/0187330 A1* | 10/2003 | Abe | 600/180 |
| 2003/0233024 A1* | 12/2003 | Ando | 600/111 |
| 2005/0010081 A1* | 1/2005 | Doguchi et al. | 600/109 |
| 2006/0082646 A1* | 4/2006 | Abe et al. | 348/68 |
| 2006/0217593 A1* | 9/2006 | Gilad et al. | 600/160 |
| 2007/0147033 A1* | 6/2007 | Ogawa et al. | 362/230 |

FOREIGN PATENT DOCUMENTS

| | | |
|---|---|---|
| JP | 64-77017 A | 3/1989 |
| JP | 63-82619 A | 4/1998 |
| JP | 2000-147615 A | 5/2000 |
| JP | 2000-166870 A | 6/2000 |
| JP | 2000-241718 A | 9/2000 |
| JP | 2003-018456 | 1/2003 |
| JP | 2004-213689 A | 7/2004 |
| JP | 2004-525573 A | 8/2004 |
| JP | 2005-192791 A | 7/2005 |
| WO | WO 02/080376 A2 | 10/2002 |

OTHER PUBLICATIONS

Chinese Official Action dated Mar. 10, 2010 with English translation.
Japanese Office Action dated Sep. 20, 2011 from corresponding Japanese Patent Application No. 2006-206830 together with partial English translation.

* cited by examiner

ENDOSCOPIC APPARATUS AND IMAGE PICKUP METHOD FOR THE SAME

CROSS-REFERENCE TO RELATED APPLICATIONS

This application is based upon and claims the benefit of priority from prior Japanese Patent Application No. 2006-206830, filed Jul. 28, 2006, the entire contents of which are incorporated herein by reference.

BACKGROUND OF THE INVENTION

1. Field of the Invention

The present invention relates to signal processing for an image pickup device provided at a distal end of an insertion portion of an endoscopic apparatus 2. Description of the Related Art An endoscopic apparatus generally has a light source (a light guide or the like) and an objective lens both attached to a distal end of an insertion portion; the light source illuminates the interior of the body cavity and the objective lens is used to capture observation images. An observation image formed by the objective lens is photoelectrically converted into an image signal by a solid image pickup device (for example, a CCD image sensor or a CMOS image sensor). The image signal is then transmitted to a camera control unit (CCU) and then subjected to various types of image processing such as white balance adjustment. The signal is finally displayed on a display section.

An observer operates an operation portion to insert the distal end of the insertion portion while bending the distal end so that the distal end conforms to the shape of the interior of the body cavity. The observer observes motion pictures and operates a shutter switch provided on an operation portion to display still images of seemingly necessary observation points.

CMOS image sensors are generally characterized by allowing single-chip manufacturing costs to be reduced more easily than CCD image sensors but being likely to distort picked-up images owing to restarting of charging immediately after reading of charges.

BRIEF SUMMARY OF THE INVENTION

The present invention provides an endoscopic apparatus that enables charges to be accumulated simultaneously with an image pickup operation performed by a CMOS image sensor to allow undistorted and non-blurred observation images to be picked up even with a quickly moving subject, as well as an image pickup method for the endoscopic apparatus.

An embodiment in accordance with the present invention provides an endoscopic apparatus comprising an endoscope main body having an insertion portion including a CMOS image sensor provided at a distal end to pick up an image of a subject illuminated by a light source in a body cavity not reached by external light, the image comprising a motion picture or a still image, and a switch coupled to the insertion portion to given an instruction to pick up a still image; a camera control unit having a control portion which, in response to the operation of the switch, performs resetting by extinguishing the light source and emitting charges accumulated in all of a plurality of pixels arranged in the CMOS image sensor in a matrix and which then performs still image pickup control by illuminating the light source in the reset state, allowing the CMOS image sensor to pick up a still image, and after the image pickup, extinguishing the light source and reading the charge from each of the pixels; and a monitor which displays an observation image comprising the picked-up motion picture or still image and information on the observation image.

An embodiment of the present invention provides an image pickup method for an endoscope observing the interior of a body cavity on the basis of a motion picture or a still image, the method comprising, before picking up the still image in a body cavity illuminated by a light source, extinguishing the light source; resetting the charges accumulated in all of a plurality of pixels arranged in a CMOS image sensor in a matrix; illuminating the light source in the reset state; and while reading the charges accumulated in the respective pixels, extinguishing the light source again and simultaneously reading the accumulated charges from all the pixels, during the same charge up period.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be described below in detail with reference to the drawings.

Figure 1:
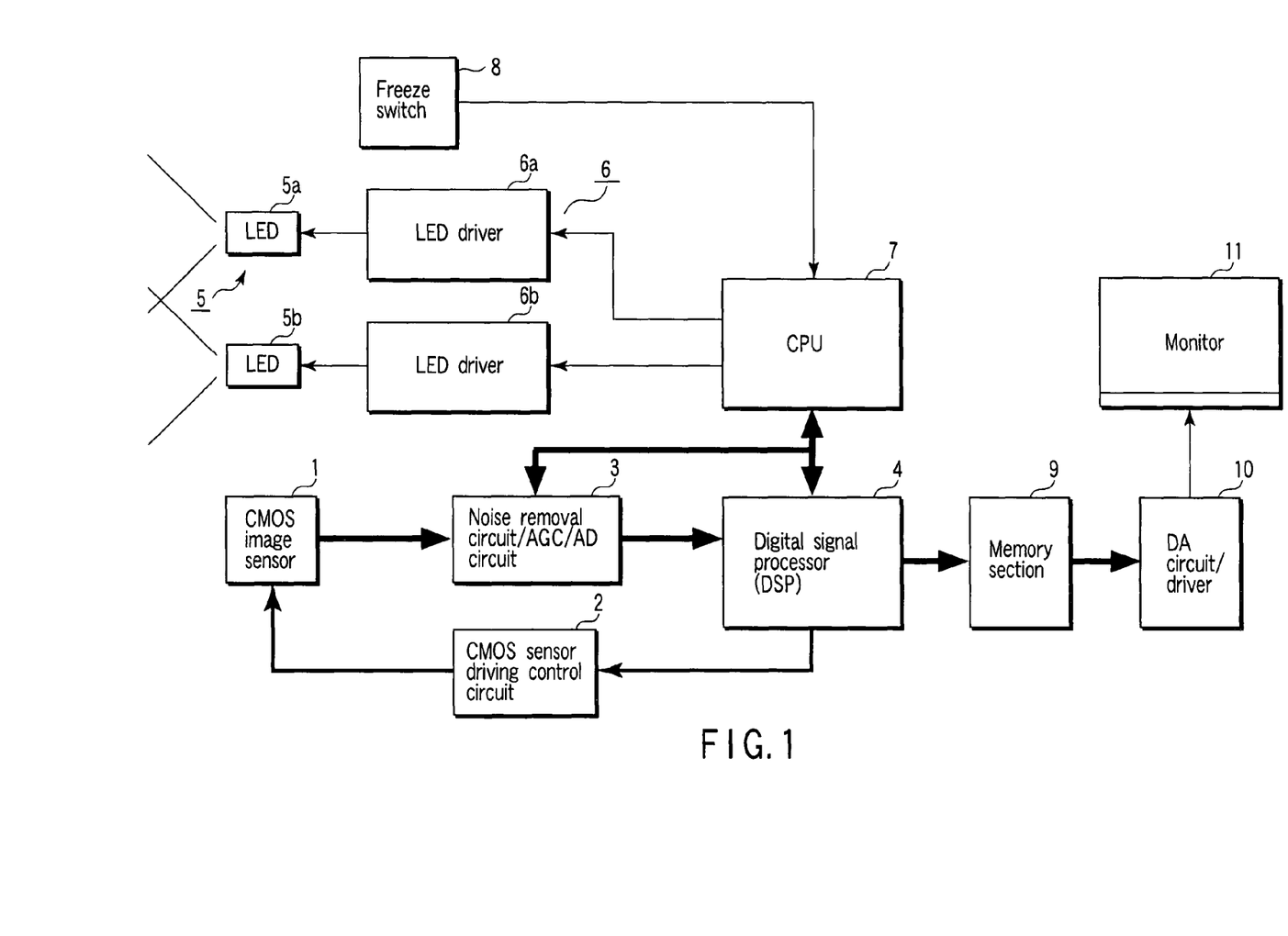
FIG. 1 is a diagram showing an example of the configuration of an image pickup system in accordance with a first embodiment.

FIG. 1 shows an example of the general configuration of an image pickup system in accordance with the present invention.

The image pickup system is composed of a CMOS image sensor 1 that picks up an image of a subject and photoelectrically converts the image into an image signal, a CMOS sensor driving control circuit 2 that drives the CMOS image sensor 1, a noise removal circuit/AGC/AD circuit 3 that performs noise removal and gain adjustment on the generated image signal to provide a digital signal, a digital signal processor (DSP) 4 that performs various types of image processing such as image synthesis and white balancing on the digital image signal, a light source 5 (LEDs 5a, 5b) that illuminates an image pickup range during an image pickup operation performed by the CMOS image sensor 1, an LED driver 6 (6a, 6b) that drivingly controls the amount of emission from the LEDs 5a, 5b, a central processing unit (CPU [control section]) 7 that controls the whole apparatus and executes calculation processes, a freeze switch 8 used to give a shutter instruction (trigger operation) in order to allow the CMOS image sensor 1 to pick up still images, a memory section 9 that stores processed image data output by DSP 4 in frame units or image units, a DA circuit/driver 10 which executes a process for displaying image data (for example, an analog process) and which outputs the data to a monitor 11, and a display monitor 11 such as a liquid crystal display which displays observation images comprising motion pictures or still images and information on the observation images (observation positions, parameters, and the like).

Figure 2:
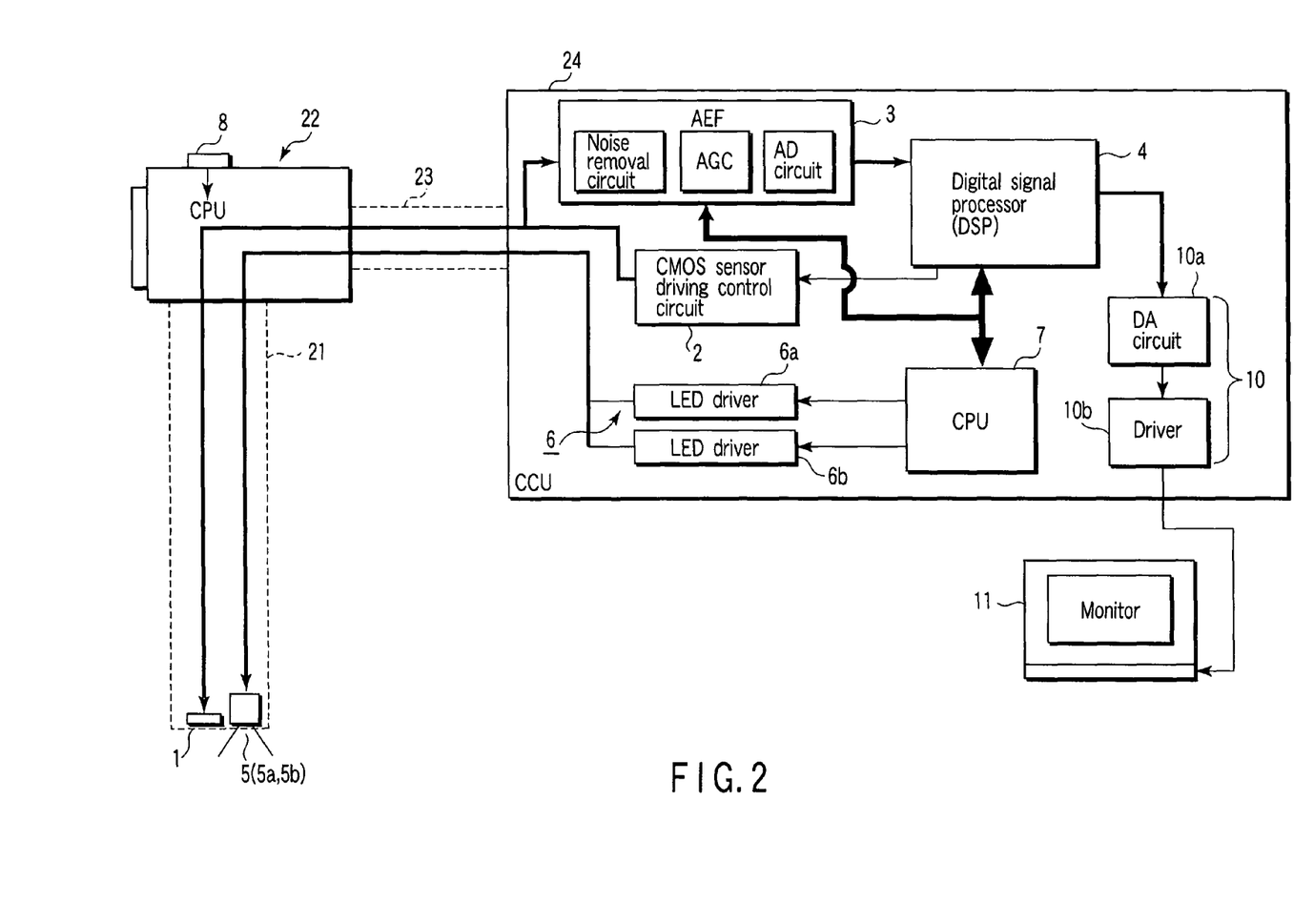
FIG. 2 is a diagram showing an example of the configuration of an endoscopic apparatus in which the image pickup system in accordance with the first embodiment is mounted.

FIG. 2 shows, as a first embodiment, an example of the configuration of an endoscopic apparatus in which the image pickup system is mounted. Components of the present embodiment similar to those shown in FIG. 1 are denoted by the same reference numerals and will not be described below.

The endoscopic apparatus is composed of an insertion portion 21 that is inserted into the body cavity (dark space) that almost no light can reach, an operation portion 22 coupled to the insertion portion 21 and having a freeze switch 8 used to give an instruction to pick up a still image, a camera control unit (CCU) 24 that drivingly controls an image pickup device and a light source to execute various types of processing on a picked-up image signal, and a monitor 11 that displays the picked-up observation image.

The endoscopic apparatus main body is mainly composed of the insertion portion 21 and the operation portion 22. A picked-up image signal and control signals including a freeze signal are propagated to CCU 24 via a cable 23 comprising a bundle of a plurality of signal wires. The endoscopic apparatus main body may be such that the insertion portion 21 is flexible and that an operation site provided in the operation portion 22 performs flexible control.

The CMOS image sensor 1, the LEDs 5a, 5b, and a forceps hole (forceps passage) are provided at a distal end of the insertion portion 21. The forceps hole is well known and will not be described below. The CMOS image sensor 1 is connected to the CMOS sensor driving control circuit 2 via the cable 23. The LEDs 5a, 5b are connected to the LED drivers 6a, 6b, respectively, via the cable 23.

For CCU 24, only its arrangements relating to image pickup are illustrated. CCU 24 comprises at least the CMOS sensor driving control circuit 2, AFE (noise removal circuit/AGC/AD circuit) 3, the DSP 4, the LED driver 6, CPU 7, the memory section 9, a DA circuit 10a, and a driver 10b (DA circuit/driver 10). The endoscopic apparatus comprises other ordinary components required to drive and which will not be described below.

In this example of the configuration of the endoscopic apparatus, LEDs 5a and 5b are provided at the distal end of the insertion portion 21. However, the LEDs 5a, 5b may be provided in the operation portion 22 or CCU 24 for the light guide unit. Further, laser diodes may be used in place of the LEDs. When a light source is provided in CCU 24, lamps that are quickly turned on and off may be used Moreover, the configuration in accordance with the present embodiment uses the single CMOS image sensor. However, the present invention is also applicable to an image pickup system that uses at least two CMOS image sensors to pick up three-dimensional images.

To pick up a still image inside the body cavity, the present embodiment first extinguishes LEDs 5a, 5b to quickly read (sweep out) charges accumulated in the pixels in the CMOS image sensor 1. The charge is thus reset to "0". This resetting is not limited to setting the charge amount to zero for all the pixels but preferably sweeps out the charges so as to set the charge amount as close to "0" as possible. Further, before a still image is picked up, all the pixels preferably have a uniform charge amount. Alternatively, a CMOS image sensor 1 comprising a global set function resets the charge amount for all the pixels. In this case, when the LEDs 5a, 5b are extinguished, almost no external light reaches the CMOS image sensor 1, located inside the body cavity, preventing charges from being accumulated in the pixels.

Using these techniques to reset the charges accumulated in the pixels eliminates the charges from all the pixels in the CMOS image sensor 1. In this reset state, the LEDs 5a, 5b are illuminated, and the CMOS image sensor 1 picks up a still image. This allows the simultaneous start of accumulation of charges in all the pixels in the CMOS image sensor 1 during the same period (exposure time).

Figure 3:
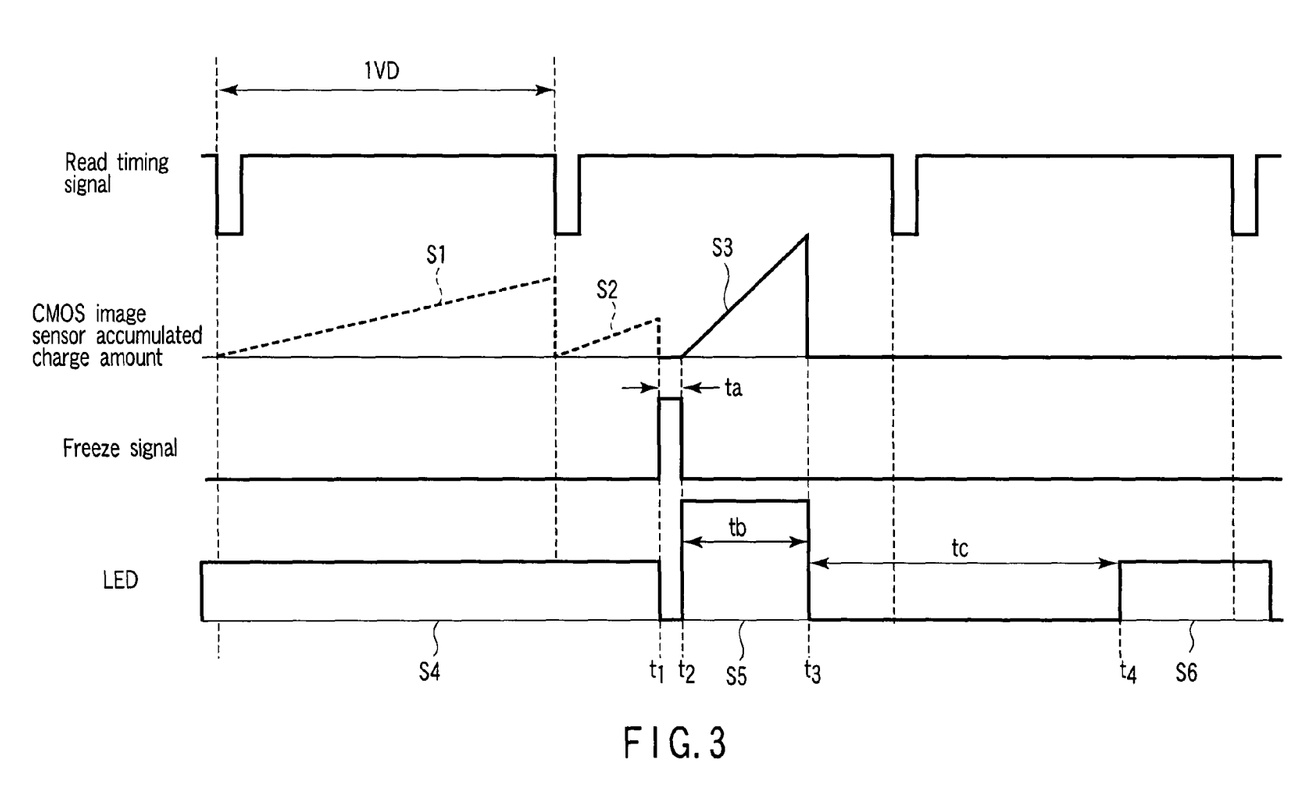
FIG. 3 is a timing chart illustrating an image pickup operation performed by the image pickup system mounted in the endoscopic apparatus.
Figure 4:
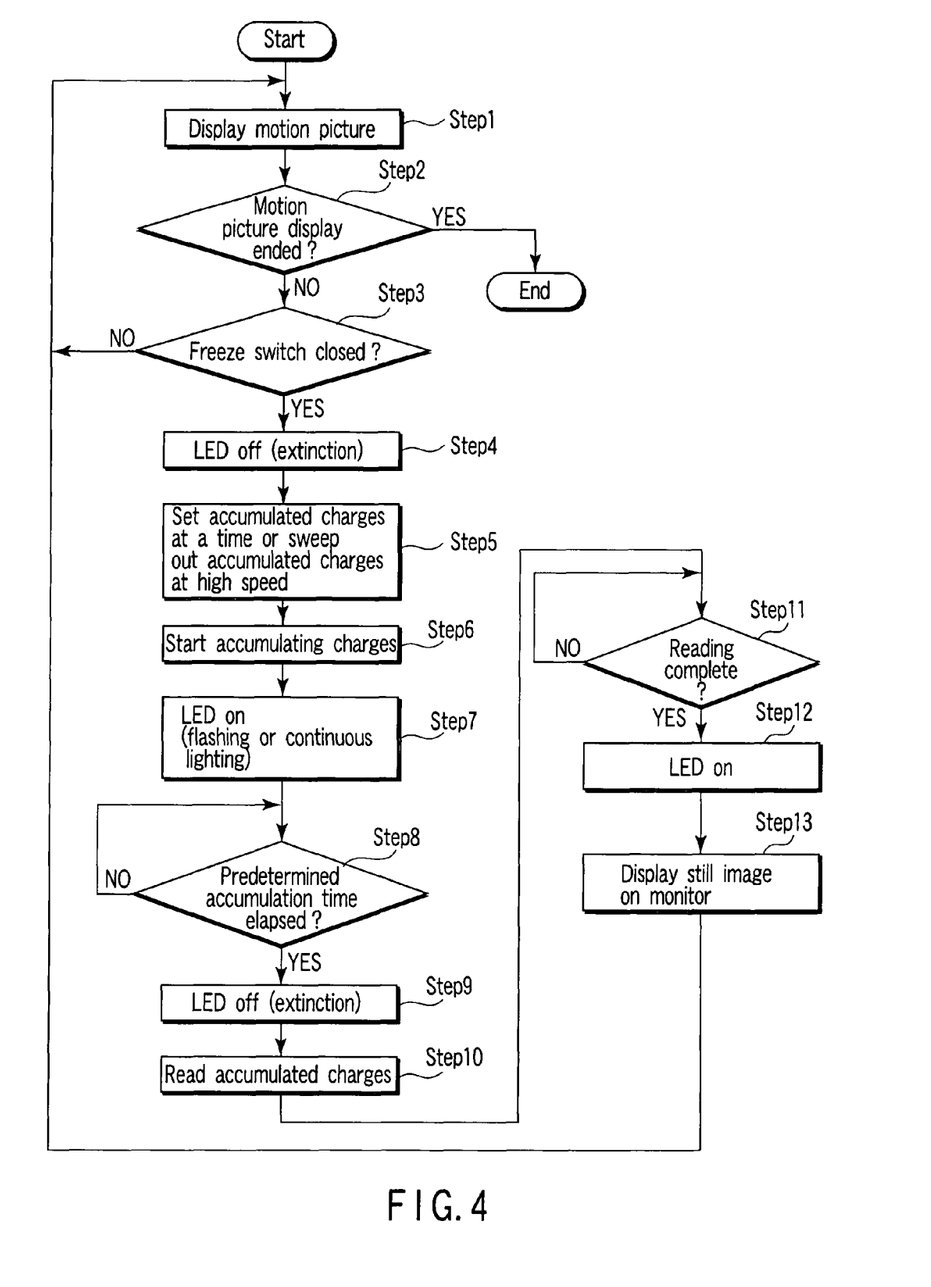
FIG. 4 is a flowchart illustrating the image pickup operation performed by the image pickup system mounted in the endoscopic apparatus.

An image pickup operation performed by this configuration will be described below in detail with reference to a timing chart shown in FIG. 3 and a flowchart shown in FIG. 4.

First, the insertion portion 21 is inserted into the body cavity. An observation image of a motion picture picked up by the CMOS image sensor 1 is displayed on the monitor 11 (step 1). The apparatus subsequently determines whether or not an operation of ending the observation of the interior of the body cavity has been performed (step S2). If the observation is to be ended, the sequence is ended. If the observation is not to be ended (NO), the apparatus determines whether or not the freeze switch 8 has been closed to pick up a still image (step 3). When the apparatus determines that the freeze switch 8 has not been closed (NO), the process returns to step 1 to continue displaying a motion picture. If the freeze switch 8 has been closed (YES), a freeze signal shown in FIG. 3 is generated and LEDs 5a and 5b are extinguished (time t1). Subsequently, accumulated charges S1, S2 are swept out of all the pixels at high speed during a period ta for resetting (step 5). Alternatively, the global set function allows the charges accumulated in all the pixels to be reset at the same time.

After the charge resetting is completed (time t2), LEDs 5a, 5b are illuminated (step 6) to simultaneously start accumulating charges in all the pixels in the CMOS image sensor 1 (step 7). The illumination may be flashing (including blinking) or continuous illumination. Illumination light S5 required to pick up a still image is designed to have an illumination light quantity larger than those S4, S6 required to display motion pictures, as shown in FIG. 3.

The apparatus determines whether or not a preset exposure time (charging period tb) has elapsed during which an estimated amount S3 of charge is accumulated in all the pixels (step 8). When the apparatus determines that the set time has elapsed (time t3) (YES), LEDs 5a, 5b are extinguished (step 9). Reading of the charges accumulated in the pixels in the CMOS image sensor 1 is started (step 10). Reading of charges includes reading of charges from all the pixels and reading, based on, for example, trimming or zooming, of charges from a pixel region of interest constituting a part of the entire pixel region. This makes it possible to easily provide an enlarged display of a site to be noted by the observer.

Now, description will be given of reading of charges from the pixels in conjunction with extinction of light. As also described in "BACKGROUND OF THE INVENTION", the CMOS image sensor cannot perform simultaneous reading on all the pixels but performs sequential reading on the basis of an XY address scheme.

Consequently, pixels from which charges are read later are subjected to light for an increased time, resulting in the accumulation of charges. Thus, in the present embodiment, before charges are sequentially read from the pixels, the LEDs 5a, 5b are extinguished. This prevents charges from being accumulated in the pixels from which charges have not been read yet. This operation allows all the pixels to be subjected to light for the same amount of time even though the charges are read at a normal speed. Consequently, undistorted observation images can be created.

The apparatus then determines whether or not the reading of the charge from each pixel has been finished (period tc) (step 11). If the reading is determined to have been finished, LEDs 5a, 5b are illuminated (step 12), and loading of motion pictures is started. At this time, for image pickup checks, picked-up still images are displayed on the monitor 11 before the motion pictures are displayed on the monitor 11 (step 13). Once the time required checking the still images on the monitor 11 elapses, the still images are automatically switched to the motion pictures. Of course, a separate switch may be operated to manually switch the still images to the motion pictures.

As described above, with the image pickup system in accordance with the first embodiment, the insertion portion 21 of the endoscope is inserted into the dark space such as the body cavity. To pick up a still image, light is turned off to reset the charges accumulated in all the pixels in the CMOS image sensor 1. The resetting eliminates the charges accumulated in the respective pixels with different charge amounts. This sets the charge amounts to zero or substantially the same value close to zero.

Further, at this time, the light source is turned on to illuminate the subject. Then, after a desired quantity of light is obtained for each pixel, the light source is turned off, and in the turned-off state, the charges accumulated in the respective pixels are read. The charge reading in the turned-off state produces exactly the same result as that of reading of charges from the image pickup device with a shutter of an electronic still camera closed after exposure. Thus, while charges are being read from the pixels, no further light is applied to the pixels from which the charges have not been read yet. This makes it possible to prevent still images from being blurred or distorted.

Moreover, if further still images are to be picked up, a process of resetting the charges accumulated in all the pixels can be omitted. That is, while charges are being read, the light is off with no charges accumulated in the pixels. Consequently, once the reading is completed, no charges are accumulated in the pixels. Thus, if further still images are to be picked up, the process of resetting the charges can be omitted. This enables the next image pickup operation to be immediately started. When still images are consecutively picked up, the charge resetting process can be omitted except the initial one. This enables the image pickup operation to be repeated in a short time. Further, each picked-up still image can be displayed on the display monitor 11. This enables images of the desired subject (site) to be picked up without the need to check motion pictures.

The image pickup system in accordance with the present embodiment is applicable to any subject environments other than the interior of the body cavity provided that the subject environment applies no light to the CMOS image sensor 1 while the light source is off. For example, an image pickup system is possible which picks up images of a subject moving through a laid pipe or the like.

Now, a second embodiment will be described with reference to the timing chart shown in FIG. 5.

Compared to the first embodiment, the present embodiment increases the quantity of light emitted by the light source, that is, LEDs 5a, 5b, per unit time to reduce the time for which charges are accumulated in the pixels in the CMOS image sensor 1. The configuration of the present embodiment is equivalent to that of the first embodiment except for the quantity of light emitted by the light source (LEDs 5a, 5b). Thus, the configuration of the present embodiment is shown by the same reference numerals as those in the first embodiment and will not be described below.

Figure 5:
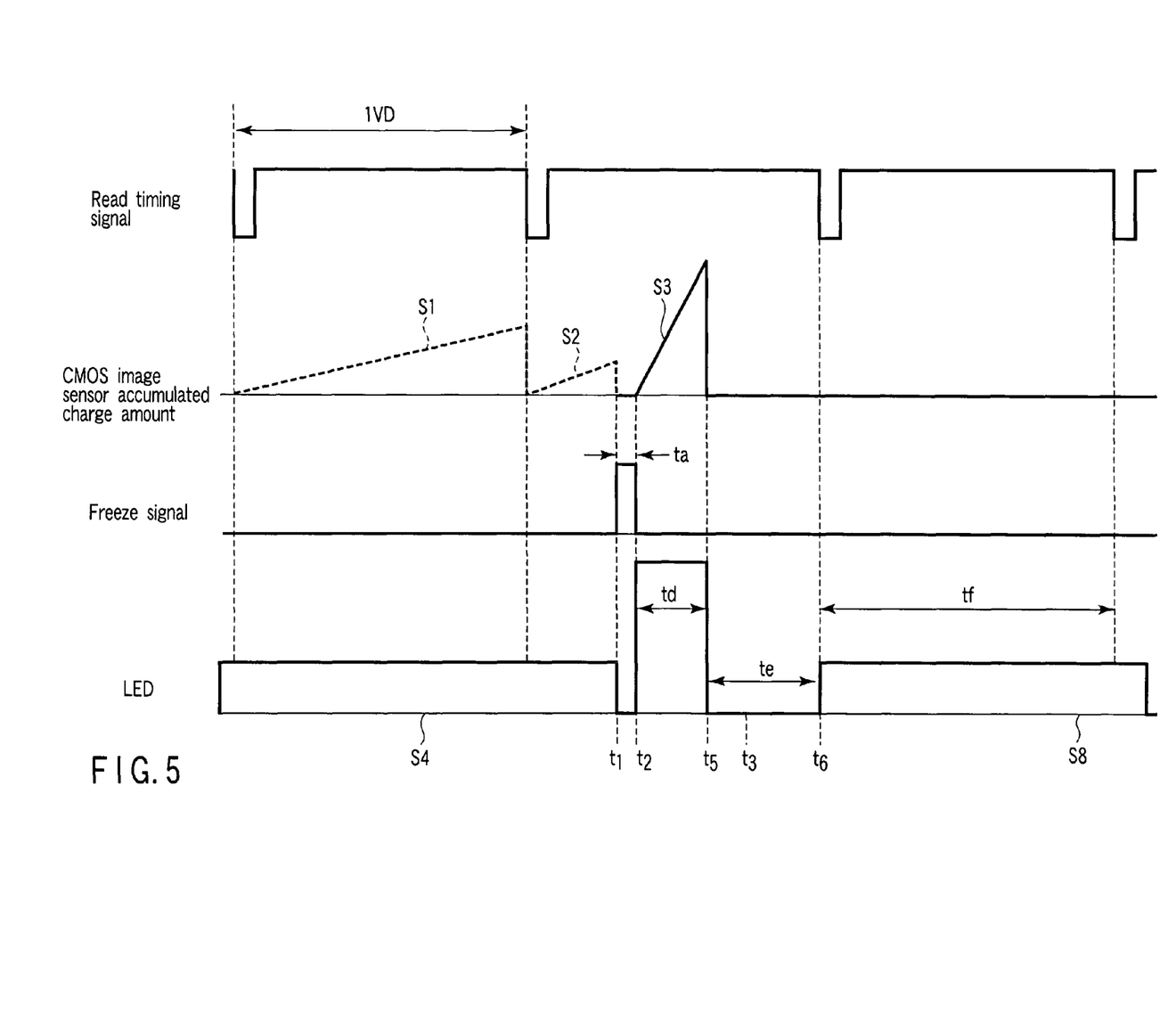
FIG. 5 is a timing chart illustrating an image pickup operation performed by an image pickup system in accordance with a second embodiment.

In the present embodiment, as shown in FIG. 5, the freeze switch 8 is closed to generate a freeze signal, while extinguishing LEDs 5a, 5b (time t1). Subsequently, during the period ta, the charges S1, S2 accumulated in all the pixels are reset. After the charge resetting is completed (time t2), LEDs 5a, 5b are illuminated to irradiate the subject with a larger quantity of illumination light than in the first embodiment. Illumination with the larger light quantity reduces the exposure time. This makes possible to further reduce the blurring and distortion of still images. The illumination may be flashing (including blinking) or continuous illumination.

Under this illumination, each pixel is charged up to a desired charge amount in a short time. In this example, as shown in FIG. 5, after the charge up period td, LEDs 5a, 5b are extinguished, and reading of the charges accumulated in the pixels in the CMOS image sensor 1 is started. Any period te after the completion of the charge reading, LEDs 5a, 5b are illuminated (time t6), and loading of motion pictures is started. At this time, as in the case of the first embodiment, picked-up still images are displayed on the monitor for checks and then switched to the motion pictures.

Besides light emission control performed by the LED driver, various methods may be used to irradiate the subject with a large quantity of illumination light. For example, light emission is controlled by selecting LED with a larger quantity of light emission or increasing the number of LEDs used. Alternatively, LEDs with large light emission may be selected so that for example, one of the two LEDs is illuminated to pick up motion pictures, while both LEDs are illuminated to pick up still images.

Figure 6:
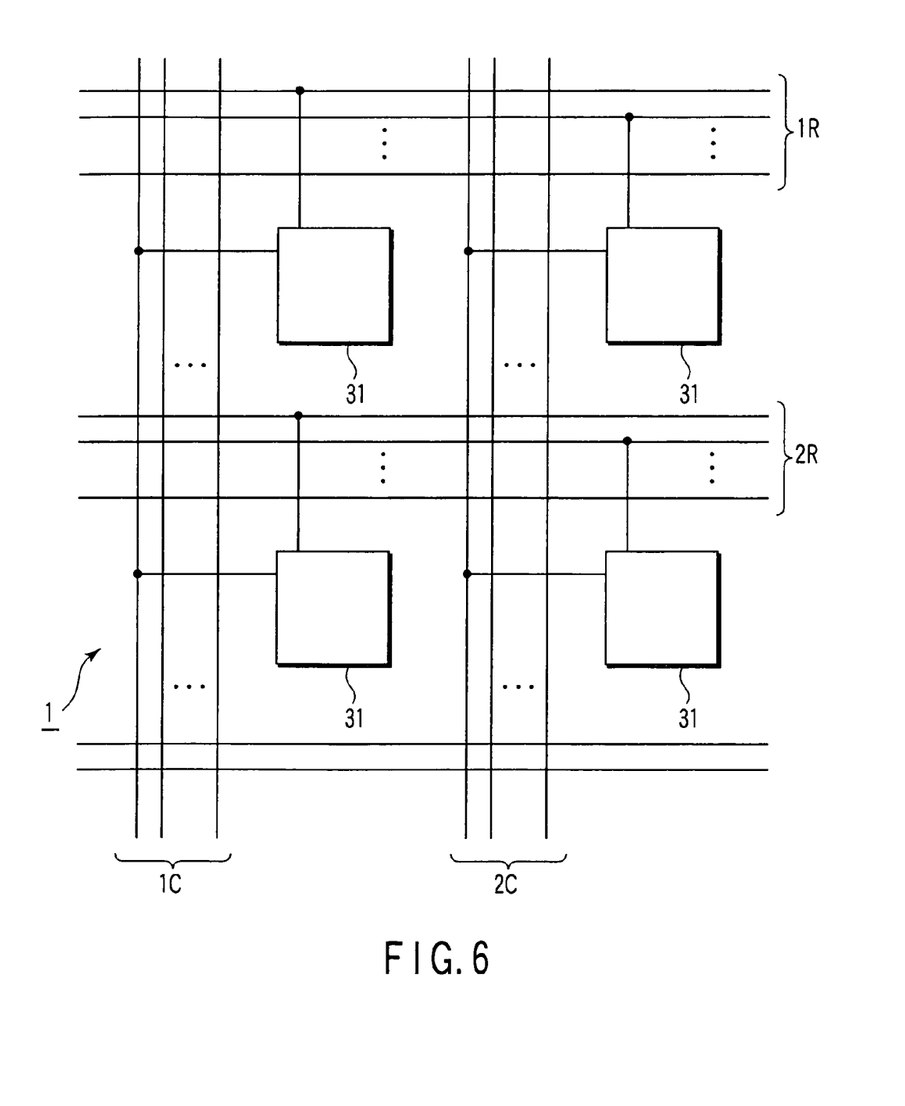
FIG. 6 is a diagram showing an example of the configuration of a CMOS image sensor in accordance with the present invention.

Further, for charge reading, the reading speed can be increased more easily for the CMOS image sensor than for CCD. As shown in FIG. 6, the CMOS image sensor is normally configured on the basis of an XY address scheme; a plurality of pixels 31 are arranged in a matrix, one row selection line is provided for each pixel row, and one column signal line is provided for each pixel column. By providing a plurality of row selection lines (1R, 2R, . . . ) and a plurality of column signal lines (1C, 2C, . . . ), which constitute the XY address scheme, it is possible to substantially simultaneously read charges from a plurality of pixels, enabling an increase in apparent reading speed. The increase in speed results in time to spare, allowing a still image to be displayed on the monitor in the succeeding field.

The present invention can provide an endoscopic apparatus that enables charges to be accumulated simultaneously with an image pickup operation performed by a CMOS image sensor to allow undistorted and non-blurred observation images to be picked up even with a quickly moving subject, as well as an image pickup method for the endoscopic apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic apparatus comprising:
an endoscope main body having an insertion portion including a CMOS image sensor provided at a distal end to pick up an image of a subject illuminated by a light source in a body cavity not reached by external light, the image comprising a motion picture or a still image, and a switch coupled to the insertion portion to input a freeze signal to give an instruction to pick up a still image;
a camera control unit having a control portion which, in response to operation of the switch, during picking up the motion picture, performs extinguishing the light source in a same frame in which the freeze signal is input and after extinguishing the light source in the same frame in which the freeze signal is input, resetting charges accumulated in all of pixels arranged in the CMOS image sensor and which after resetting the charges accumulated in the CMOS image sensor in the same frame in which the freeze signal is input, then controls the light source to illuminate the body cavity, at a greater illumination amount than an illumination amount at picking up the motion picture, for an illumination period shorter than an illumination period at picking up the motion picture, exposing the pixels in the CMOS image sensor, and extinguishing the light source after exposing the pixel in the same frame in which the freeze signal is input, and reading the charge from each of the pixels while the light source is extinguished after exposing the pixels in the same frame in which the freeze signal is input; and
a monitor which displays an observation image comprising the picked-up motion picture or still image and information on the observation image.

2. The endoscopic apparatus according to claim 1, wherein the light source is provided at a distal end of the insertion portion or in the endoscope main body and comprises a light emitting diode to irradiate the subject with illumination light based on lighting or blinking.

3. The endoscopic apparatus according to claim 1, wherein the light source is provided at a distal end of the insertion portion or in the operation portion and comprise a laser diode to irradiate the subject with illumination light based on lighting or blinking.

4. The endoscopic apparatus according to claim 1, wherein a plurality of row selection lines and a plurality of column signal lines are provided for each pixel row and each pixel column, respectively, the row selection lines and the column signal lines being used to read, in accordance with an XY address scheme, charges from the plurality of pixels arranged in a matrix and constituting the CMOS image sensor.

5. The endoscopic apparatus according to claim 1, wherein at least two of the CMOS image sensor are arranged in the insertion portion to pick up a three-dimensional image.

6. An endoscopic apparatus comprising:
a CMOS image sensor which picks up an image of a subject illuminated in a dark space not reached by external light and which photoelectrically converts the image into an image signal;
a CMOS sensor driving control circuit which drives the CMOS image sensor;
a signal adjustment circuit which performs a signal adjustment and digitization process including noise removal on the generated image signal;
a digital signal processing section which executes image processing on the digital image signal;
a memory section which stores the image signal subjected to image processing in frame units or image units;
a light source which illuminates an image pickup range while the CMOS image sensor is picking up an image;
a light source driving section which controllably drives the quantity of light emission from the light source;
a central processing section which controls the whole apparatus and which executes arithmetic processing;
a freeze switch which gives a shutter instruction to allow the CMOS image sensor to pick up a still image;
a memory section in which image data output by the digital signal processing section;
a display driving section which executes processing required to display the image data; and
a monitor which displays an image signal output by the display driving section,
wherein before the freeze switch is used to pick up a still image during picking up the motion picture, the apparatus extinguishes the light source in a same frame in which the freeze signal is input, resets charges accumulated in respective pixels in the CMOS image sensor, illuminates the light source in the reset state, at a greater illumination amount than an illumination amount at picking up the motion picture, for an illumination period shorter than an illumination period at picking up the motion picture, and allows the CMOS image sensor to pick up a still image, and after the image pickup and while the charge is being read from each pixel, the apparatus performs operations until keeping the light source off and controls simultaneity of the accumulation of pixels in the CMOS image sensor so that no further charges are accumulated in the pixels from which the charges have not been read yet.

7. An image pickup method for an endoscope observing the interior of a body cavity on the basis of a motion picture or a still image, the method comprising:
before picking up the still image in a body cavity illuminated by a light source, extinguishing the light source;
resetting the charges accumulated in all of a plurality of pixels arranged in a CMOS image sensor in a matrix;
illuminating the light source in the reset state; and
while reading the charges accumulated in the respective pixels, extinguishing the light source again and simultaneously reading the accumulated charges from all the pixels, during the same charge up period.

8. The image pickup method according to claim 7, wherein the reading of the charges from the CMOS image sensor comprises reading of charges from all the pixels and reading, based on trimming or zooming, of charges from a pixel region of interest constituting a part of the entire pixel region.

* * * * *